United States Patent [19]
Hillstead

[11] Patent Number: 5,098,440
[45] Date of Patent: Mar. 24, 1992

[54] OBJECT RETRIEVAL METHOD AND APPARATUS

[75] Inventor: Richard A. Hillstead, Miami, Fla.

[73] Assignee: Cordis Corporation, Miami Lakes, Fla.

[21] Appl. No.: 567,199

[22] Filed: Aug. 14, 1990

[51] Int. Cl.⁵ .................. A61M 25/00; A61B 17/00
[52] U.S. Cl. .................... 606/108; 606/113; 604/52; 604/53; 128/4; 128/7
[58] Field of Search .......... 604/52, 53, 281, 282, 604/105; 606/198, 159, 108, 113, 140, 142; 128/749, 772, 4-5, 7, 8

[56]  References Cited

U.S. PATENT DOCUMENTS

| | | | |
|---|---|---|---|
| 529,936 | 11/1894 | McNalley | 606/113 |
| 1,127,948 | 2/1915 | Wappler | 128/7 |
| 2,767,703 | 10/1956 | Nieburgs | 128/749 |
| 3,060,972 | 10/1962 | Sheldon | 128/772 |
| 3,958,576 | 5/1976 | Komiya | 606/113 |
| 4,198,960 | 4/1980 | Utsugi | 128/7 |
| 4,655,217 | 4/1987 | Reed | 606/159 |
| 4,737,142 | 4/1988 | Heckele | 604/282 |
| 4,913,141 | 4/1990 | Hillstead | |

*Primary Examiner*—Stephan C. Pellegrino
*Assistant Examiner*—Glenn K. Dawson
*Attorney, Agent, or Firm*—Watts, Hoffmann, Fisher & Heinke Co.

[57]  ABSTRACT

Method and apparatus for retrieving an object such as a stent from a subject. A catheter supports two wire loops that can be manipulated from outside the subject to engage the object. By manipulating the catheter and the wire loops, the object can be captured and drawn inside a guide catheter through which the catheter is inserted. The catheter and attached stent can then be pulled from the subject.

6 Claims, 2 Drawing Sheets

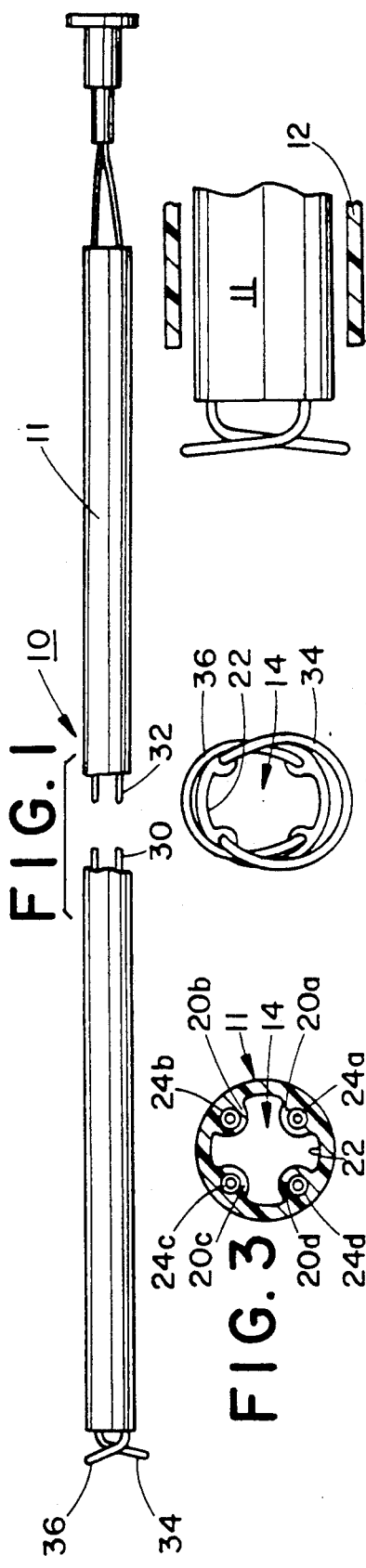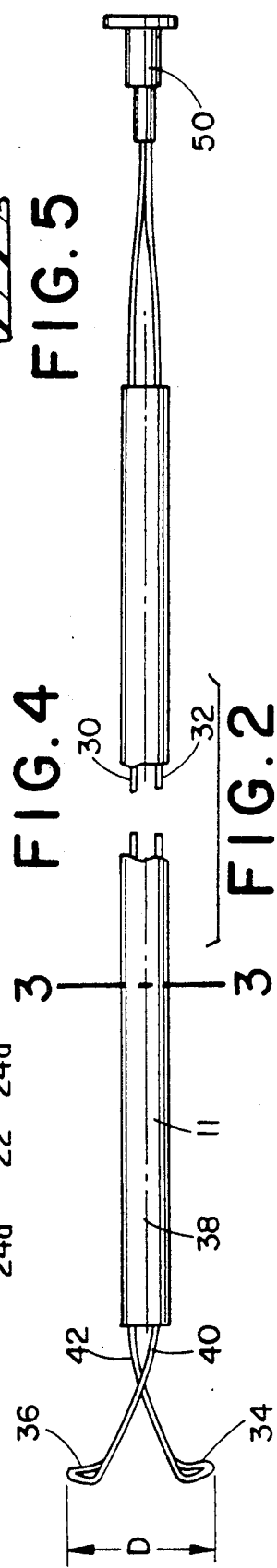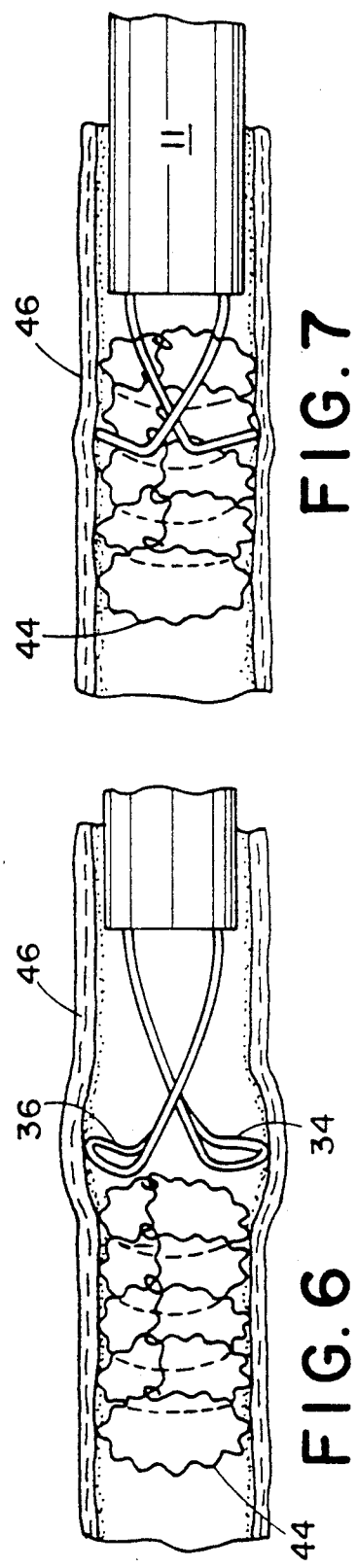

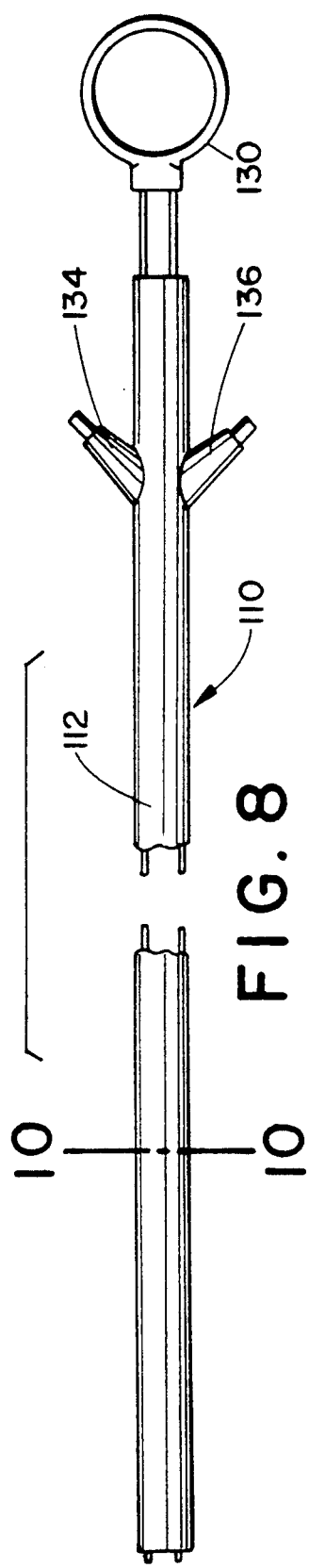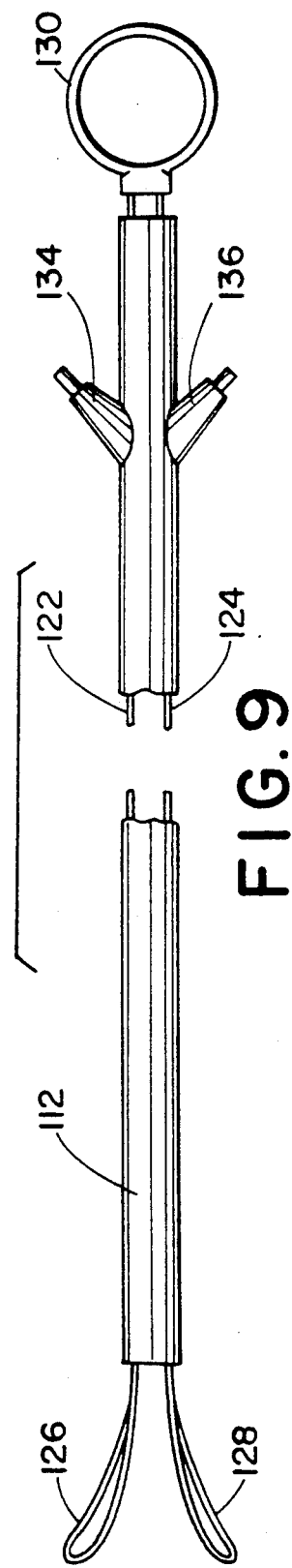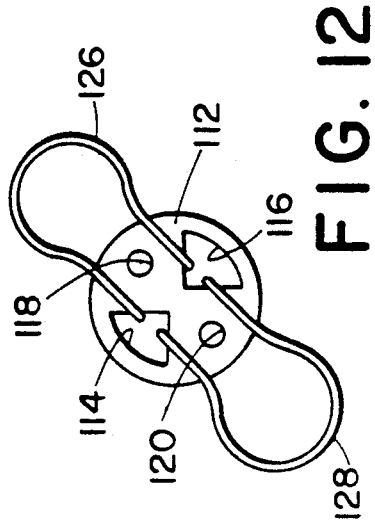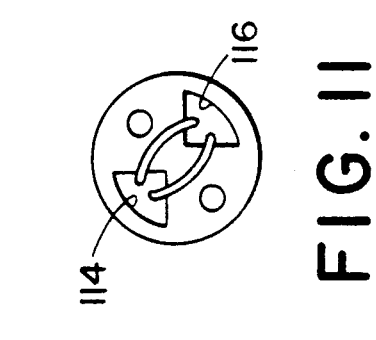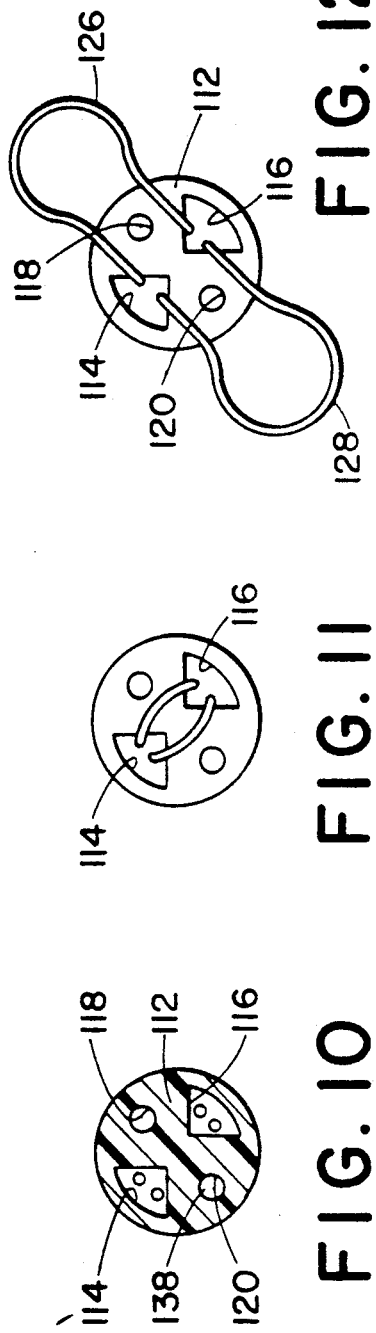

OBJECT RETRIEVAL METHOD AND APPARATUS

FIELD OF THE INVENTION

The present invention concerns a retrieval device for repositioning and/or removing an object from a vessel, particularly a blood vessel.

BACKGROUND ART

A common practice in treating vascular diseases is to place a stent within a subject vessel. This allows the vessel to heal as the stent reinforces the vessel's inner walls. The stent also may help in re-establishing fluid flow through the vessel.

Stent placement can be temporary or permanent. If it is temporary, the stent helps in reconstructing or repairing the vessel and is then moved from the subject. The repaired vessel then functions normally without stent interaction with the vessel. In certain instances an improperly positioned stent must be removed from the vessel and either repositioned or replaced. This is particularly possible in those instances in which the stent is launched into the vessel without control over its ultimate position. If, in the attending physician's opinion, the stent should be repositioned and/or removed subsequent to this placement, some mechanism must be utilized to retract or retrieve the stent.

One known procedure for stent removal is surgically removing the stent from the vessel. It is one object of the invention to achieve a less traumatic retrieval and/or repositioning mechanism particularly suited for use with a stent but having application in maneuvering any object within a vessel.

DISCLOSURE OF THE INVENTION

The present invention concerns apparatus and method for moving an object within a subject vessel and includes an elongated catheter having a throughpassage extending through a catheter body. An object engaging member is movable in a transverse direction relative the elongated catheter body and includes a distal end for engaging the object, a proximal end for controllably manipulating the distal end from outside the subject, and an intermediate portion coupling the proximal and distal ends. The intermediate portion is shielded from contact with the vessel by the body of the elongated catheter. The distal end of the object engaging member forms a loop that extends outward into the vessel beyond the distal end of the catheter body for contacting the object. By manual manipulation of the proximal end the object can be captured and repositioned or removed.

Wherein the invention is used in repositioning a stent, the looped portion of the object engaging member slips over the stent so that as the proximal end is retracted, the stent is captured. Subsequent to this capture, the catheter can be withdrawn into a guide catheter used in positioning the catheter within the subject.

Alternate embodiments of apparatus constructed in accordance with the invention are disclosed. These embodiments include structure for supporting a fiber optic light pipe for monitoring the position of an object within a vessel. The preferred configuration includes two wires bent to form two loops that extend from the end of the catheter. The wires are also bent near their distal ends to criss-cross each other.

By manipulating the proximal end of the two wires, the loops can be extended into the vessel to engage the object. As the two wires are retracted by manually pulling on the wires, the criss-cross loops are both drawn into the catheter body and tightened down on the object. The act of entering the catheter body causes the loop to straighten and engage the object with a greater force.

Other objects, advantages and features of the invention will become better understood from the detailed description of a preferred embodiment which is described in conjunction with the accompanying drawings.

BRIEF DESCRIPTION OF THE DRAWINGS

FIG. 1 is an elevational view of a catheter constructed in accordance with the present invention;

FIG. 2 is an elevational view of the catheter showing two distally formed loops extending outwardly away from the body of the catheter;

FIG. 3 is a sectioned view of the catheter as seen from the view 3—3 in FIG. 2;

FIG. 4 is an end elevational view showing a distal end of the FIG. 1 catheter;

FIG. 5 is an enlarged partially end view showing the FIG. 1 catheter with object engaging loops retracted in towards the catheter body;

FIG. 6 is an elevational view showing a catheter approaching a stent located within a blood vessel;

FIG. 7 is a distal view of the catheter showing crossed loops engaging the stent for retracting the stent from the vessel;

FIG. 8 is an elevational view of an alternate embodiment of an object removal device constructed in accordance with the invention;

FIG. 9 is an elevational view of the FIG. 8 catheter showing distally positioned object engaging loops extended outwardly from the catheter body;

FIG. 10 is a section view of the catheter as seen from the plane defined by the line 10—10 in FIG. 8;

FIG. 11 is an end view of the FIG. 8 catheter showing a distal end of the catheter with the object engaging wires retracted inward toward the catheter body; and FIG. 12 is an end elevational view showing the catheter with the object engaging wire extended away from the catheter body.

BEST MODE FOR CARRYING OUT THE INVENTION

Turning now to the drawings, FIG. 1 illustrates an elongated catheter 10 specifically constructed for retracting or moving an object within a subject vessel. The preferred use of the catheter depicted in FIG. 1 is for repositioning or removing a stent from within a blood vessel. For this application, a catheter body 11 has a length that allows the catheter to be inserted into the subject and routed to the vicinity of the stent and manipulated from outside the subject by an attending physician. Techniques are known in the prior art for positioning catheters within a subject and these techniques typically involve utilization of a guide wire and contrast medium to allow the attending physician to monitor progress of the catheter as it is inserted and withdrawn. In many applications, the catheter 10 is inserted after a so-called guide catheter 12 (FIG. 5) is first inserted into the subject and the catheter 10 routed through a center passageway of the guide catheter.

FIG. 3 is a cross-section view of the catheter body 11 showing an internal throughpassage 14 which extends the length of the catheter body. Four curved ribs 20a-20d extend inwardly from a catheter inner wall 22 at regular intervals about the circumference of the catheter body. These ribs 20a-20d also extend the length of the catheter body from a proximal to a distal end. Four small diameter passageways 24a-24d extend through the ribs in the catheter body and accommodate the back and forth movement of two elongated wires 30, 32 that extend through the catheter body 11.

At a distal end of the catheter 10 the wires 30, 32 are bent to form curved loops 34, 36. As seen most clearly in FIG. 2, the wires are also bent at positions 40, 42 proximal of the two loops 34, 36. This bend in the two wires 30, 32 causes the two loops 34, 36 to criss cross and extend outward away from a center axis 38 of the catheter body.

FIGS. 6 and 7 depict the operation of the catheter 10 in retrieving a stent within a subject. As seen in FIG. 6, a generally cylindrical stent 44 constructed in accordance with the teachings of U.S. Pat. No. 4,856,516 to Hillstead is positioned within a subject vessel 46. The catheter 10 has been inserted into the vessel by an attending physician and the two wire loops 34, 36 are pushed outward into the vessel. This is accomplished by manually manipulating a proximally located knob 50 (FIG. 2) connected to the wires. By maneuvering this knob the physician can control the relative position of the loops 34, 36 with respect to a distal end of the catheter. Both the stent 44 and the wires 30, 32 are radioopaque so that as the loops 34, 36 are positioned relative to the stent, the attending physician can monitor this relative positioning.

As seen in FIGS. 2 and 6, with the loops 34, 36 fully extended, the bends in the wire cause the loops 34, 36 to move outwardly away from the center axis of the catheter body to a position defining a capture diameter D greater than the outside diameter of the stent 44. This capture diameter allows the physician to push both catheter and loop into the subject until the loop 34, 36 overlies the stent 44. With the loops overlying the stent 44, the physician then pushes the catheter body 11 further into the vessel to the position shown in FIG. 7. As the catheter body 11 slides over the elongated wires 30, 32 the catheter body straightens the bends 40, 42 in the wire causing the two loops 34, 36 to move toward the center axis of the catheter body and engage the stent.

As seen in FIG. 5, a minimal radius formed by the loops 34, 36 is on the order of the diameter of the catheter. In this configuration the stent 44 can be securely attached to the catheter body for movement therewith.

The captured stent 44 can be retracted with the catheter 10 into the guide catheter 12 or repositioned within the vessel. Bringing the stent 44 inside the guide catheter 12 avoids moving the stent 44 along an extended travel path within the subject vessel. In operation, the stent 44 is engaged by the loops 34, 36, retracted by manual movement of both the catheter body and manipulator from outside the subject into the guide catheter 12 and then withdrawn as the guide catheter 12 is removed from the subject.

Techniques are known in the prior art for fabricating catheters from suitable plastic materials. These techniques also involve known procedures for forming throughpassages such as the center throughpassage 14 and wire accommodating throughpassages 24a-24d. Representative patents illustrating these techniques are U.S. Pat. Nos. 3,485,234 and 3,585,707 to Stevens. The disclosure of these patents is incorporated herein by reference.

An alternate construction of a catheter 110 for retracting an object from a vessel is depicted in FIGS. 8-12. The catheter body 112 is seen in FIG. 10 to include four throughpassages 114, 116, 118, 120 that extend the length of the catheter.

Two passageways 114, 116 route elongated wires 122, 124 through the length of the catheter body 112. The wires 122, 124 form loops 126, 128 that extend distally beyond the end of the catheter body 112. A pull ring 130 at the proximal end of the catheter 110 allows the physician to manipulate the two loops 126, 128 and either extend them further into the vessel to engage an object such as a stent or retract them into the catheter body to secure the object to the catheter. In the configuration shown in FIGS. 8-12, a stent is typically captured by manual manipulation of the catheter body 112 and ring 130 and then pulled into a guide catheter for removal from the subject.

Two catheter side branches 134, 136 extend away from the catheter body 112 at a position which remains outside the subject. The branch 134 defines an opening for radio-opaque material to be injected into the catheter body and along the passageway 118. The second passageway 120 accommodates a fiber optic light pipe 138 which enters the catheter through the second branch 136. The fiber optic light pipe extends through the catheter body to the catheter's distal end and facilitates the viewing of the object within the subject.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

I claim:

1. An apparatus for moving an object within a subject vessel comprising:
   a) an elongated catheter having a catheter body defining body between two proximal openings that remain outside the subject and two distal openings that open outward from a distal end of said catheter body;
   b) an object engaging member comprising wire means, said wire means further comprising first and second elongated wires bent to form first and second loops; each of said loops bridge the two distal openings and connect first and second wire segments that extend through the two passageways, exit the two proximal openings of the catheter body, and are movable along a transverse direction of said elongated catheter; and
   c) manipulator means connected to the first and second wire segments of each elongated wire outside the catheter body for extending and retracting the loops beyond a distal end of said elongated catheter to contact and to gain control of an object within the vessel.

2. The apparatus of claim 1 wherein the first and second wires are bent just proximal the loops causing the loops to criss-cross each other when extended from the catheter body and to engage the object as the wires are drawn into the passageways.

3. A method for movably engaging an object within a subject vessel comprising the steps of:
 a) bending two wires to form an elongated object engaging member, each wire having a loop that connects two elongated segments;
 b) routing the elongated segments of each wire through passageways in a catheter body so the loops extend out a distal catheter end and a manipulatable portion of the elongated segments extends out a proximal catheter end;
 c) inserting the catheter into the subject and routing the catheter's distal end to the vicinity of the object; and
 d) manipulating the loops from outside the subject by maneuvering the catheter and said object engaging member to capture the object with the loops.

4. The method of claim 3 wherein the step of inserting the catheter is performed by first inserting a guiding catheter into the subject.

5. The method of claim 4 wherein once the object is captured it is withdrawn inside the guiding catheter.

6. The method of claim 3 wherein the manipulating step is performed while viewing the object through a fiber optic light pipe extending through the catheter body.

* * * * *